(12) United States Patent
Gutzler et al.

(10) Patent No.: US 11,969,535 B2
(45) Date of Patent: Apr. 30, 2024

(54) CONNECTOR ASSEMBLY AND METHODS OF USE

(71) Applicant: CYTOSORBENTS CORPORATION, Monmouth Junction, NJ (US)

(72) Inventors: Dominik Gutzler, Ebersberg (DE); Wei-Tai Young, Monmouth Junction, NJ (US)

(73) Assignee: CytoSorbents Corporation, Monmouth Junction, NJ (US)

( * ) Notice: Subject to any disclaimer, the term of this patent is extended or adjusted under 35 U.S.C. 154(b) by 764 days.

(21) Appl. No.: 16/645,965

(22) PCT Filed: Sep. 13, 2018

(86) PCT No.: PCT/US2018/050791
§ 371 (c)(1),
(2) Date: Mar. 10, 2020

(87) PCT Pub. No.: WO2019/055588
PCT Pub. Date: Mar. 21, 2019

(65) Prior Publication Data
US 2020/0276381 A1    Sep. 3, 2020

Related U.S. Application Data

(60) Provisional application No. 62/558,412, filed on Sep. 14, 2017.

(51) Int. Cl.
*A61M 1/36*   (2006.01)
*A61M 1/16*   (2006.01)
(Continued)

(52) U.S. Cl.
CPC ........ *A61M 1/3666* (2013.01); *A61M 1/1698* (2013.01); *A61M 1/3679* (2013.01);
(Continued)

(58) Field of Classification Search
CPC . A61M 1/3666; A61M 1/3622; A61M 1/3623
See application file for complete search history.

(56) References Cited

U.S. PATENT DOCUMENTS

| | | | |
|---|---|---|---|
| 4,256,104 A | 3/1981 | Muetterties et al. |
| 4,540,399 A | 9/1985 | Litzie et al. |

(Continued)

FOREIGN PATENT DOCUMENTS

| | | |
|---|---|---|
| DE | 20212767 U1 | 11/2002 |
| JP | H05-245194 A | 9/1993 |

(Continued)

OTHER PUBLICATIONS

European Patent Application No. 18856950.3; Extended Search Report; dated May 25, 2021; 9 pages.

(Continued)

*Primary Examiner* — Susan S Su
*Assistant Examiner* — Ted Yang
(74) *Attorney, Agent, or Firm* — BakerHostetler

(57) ABSTRACT

Connector assemblies and methods of replacing components in an extra-corporeal circuit (ECC) system are disclosed. A connector assembly for use in an ECC system includes a tubular body having an inner surface defining a lumen extending through the tubular body with the lumen extending along a longitudinal axis, a first connection interface in fluid communication with the lumen, a second connection interface in fluid communication with the lumen, and a plurality of closure mechanisms, each closure mechanism being configured to occlude the lumen.

17 Claims, 18 Drawing Sheets

(51) Int. Cl.
*A61M 39/24* (2006.01)
*A61M 39/28* (2006.01)

(52) U.S. Cl.
CPC ............ *A61M 39/24* (2013.01); *A61M 39/28* (2013.01); *A61M 1/3623* (2022.05); *A61M 2202/0415* (2013.01)

(56) References Cited

U.S. PATENT DOCUMENTS

| | | | |
|---|---|---|---|
| 5,391,142 A * | 2/1995 | Sites | A61M 60/546 604/6.14 |
| 5,409,612 A | 4/1995 | Maltais et al. | |
| 5,421,813 A * | 6/1995 | Ohnishi | A61M 1/3486 137/599.14 |
| 6,206,851 B1 | 3/2001 | Prosl | |
| 6,890,316 B2 | 5/2005 | Rawles et al. | |
| 7,892,197 B2 * | 2/2011 | Folden | A61M 1/3643 604/4.01 |
| 8,105,265 B2 | 1/2012 | Demers et al. | |
| 2002/0151834 A1 | 10/2002 | Utterberg | |
| 2003/0204127 A1 | 10/2003 | Rawles et al. | |
| 2004/0015042 A1 | 1/2004 | Vincent et al. | |
| 2004/0220509 A1 | 11/2004 | Olsen | |
| 2005/0045548 A1 | 3/2005 | Brugger et al. | |
| 2005/0182349 A1 * | 8/2005 | Linde | A61M 1/3489 604/4.01 |
| 2006/0148742 A1 * | 7/2006 | Kaye | C12N 9/14 514/44 A |
| 2009/0112146 A1 * | 4/2009 | Wratten | A61M 1/3472 604/5.04 |
| 2010/0192686 A1 | 8/2010 | Kamen et al. | |
| 2011/0272337 A1 | 11/2011 | Palmer | |
| 2013/0102975 A1 | 4/2013 | Lamb | |
| 2014/0271357 A1 * | 9/2014 | Samolyk | A61M 1/3667 422/45 |
| 2016/0030656 A1 | 2/2016 | Eikelmann et al. | |

FOREIGN PATENT DOCUMENTS

| | | |
|---|---|---|
| JP | 2003-518964 A | 6/2003 |
| JP | 2005-518491 A | 6/2005 |
| JP | 2007-516038 A | 6/2007 |
| RU | 2027446 C1 | 1/1995 |

OTHER PUBLICATIONS

International Patent Application No. PCT/US2018/050791; Int'l Search Report and the Written Opinion; dated Feb. 15, 2019; 27 pages.

International Patent Application No. PCT/US2018/050791; Int'l Preliminary Report on Patentability; dated Mar. 26, 2020; 11 pages.

* cited by examiner

CONNECTOR ASSEMBLY AND METHODS OF USE

CROSS-REFERENCE TO RELATED APPLICATIONS

This application is the National Stage Application of International Patent Application No. PCT/US2018/050791 filed Sep. 13, 2018 which claims the benefit of U.S. Provisional Application No. 62/558,412, filed Sep. 14, 2017, the entirety of which is incorporated herein for any and all purposes.

TECHNICAL FIELD

The present disclosure relates generally to connectors in fluid flow systems, and more particularly to connector assemblies for hot-swapping components in extra-corporeal circuit (ECC) systems.

BACKGROUND

Extra-corporeal circuit (ECC) systems are often used to provide prolonged cardiac and respiratory support to patients in situations where the heart and lungs are unable to provide adequate perfusion and gas exchange. However, existing ECC machines do not offer effective methods of purifying blood while continuously operating the ECC system. Existing systems have purification components that cannot be safely and effectively introduced, removed, or replaced, without dangerously-high risks of blood loss, air intake, or contamination of the fluid.

SUMMARY

Disclosed herein are devices and methods for introducing, removing, and replacing components of an extra-corporeal circuit (ECC) system during continued operation of the ECC system. The disclosed methods and devices may be used with any suitable pump-driven or pressure-gradient-driven ECC system, such as extra-corporeal membrane oxygenation (ECMO) systems, CRRT Dialysis, hemoperfusion, cardiopulmonary bypass (CPB), and other similar setups. While specific embodiments may be directed to a particular ECC system (e.g. ECMO), it will be understood that the disclosure is not limited to only the exemplified system.

According to one embodiment, a connector assembly for use in an extracorporeal membrane oxygenation (ECMO) system includes a tubular body having an inner surface that defines a lumen extending through the tubular body. The lumen extends along a longitudinal axis. The connector assembly has a first connection interface in fluid communication with the lumen and a second connection interface in fluid communication with the lumen. The connector assembly further includes a plurality of closure mechanisms, each of the plurality of closure mechanisms being configured to occlude the lumen.

According to another embodiment, a method of modifying a component in an extracorporeal membrane oxygenation (ECMO) system during operation of the ECMO system includes switching a first closure mechanism from an open configuration to a closed configuration such that fluid flow through the lumen is obstructed by the first closure mechanism. The method further includes the step of switching a second closure mechanism from an open configuration to a closed configuration such that fluid flow through the lumen is obstructed by the second closure mechanism. The method also includes the step of disconnecting the component from the ECMO system. The component in the ECMO system is in fluid communication with a connector having a tubular body with an inner surface that defines a lumen extending therethrough.

According to another embodiment, a method of operating an extracorporeal membrane oxygenation (ECMO) system having a purification component in fluid communication with the ECMO system via a connector assembly includes introducing a fluid from a fluid source to the ECMO system, operating a pump within the ECMO system to move the fluid through the purification component and an oxygenation component, and moving the fluid to a fluid destination out of the ECMO system. The connector assembly has a tubular body with an inner surface defining a lumen therethrough, a first closure mechanism, and a second closure mechanism.

According to another embodiment, a method of operating an active bypass system with an extracorporeal membrane oxygenation (ECMO) system having a pump and an oxygenation component includes connecting an inlet of the active bypass system to the ECMO system via a first connector assembly, connecting an outlet of the active bypass system to the ECMO system via a second connector assembly, and operating the active bypass system and the ECMO system. The first connector assembly and the second connector assembly each have a tubular body with an inner surface that defines a lumen extending therethrough. Each connector assembly further has a first closure mechanism and a second closure mechanism, each of the first and second closure mechanisms being configured to have an open configuration in which the first and second closure mechanisms, respectively, do not obstruct the lumen and a closed configuration in which the first and second closure mechanisms, respectively, obstruct the lumen.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. Furthermore, the drawings are not necessarily drawn to scale. In the drawings.

DETAILED DESCRIPTION OF ILLUSTRATIVE EMBODIMENTS

Figure 1:
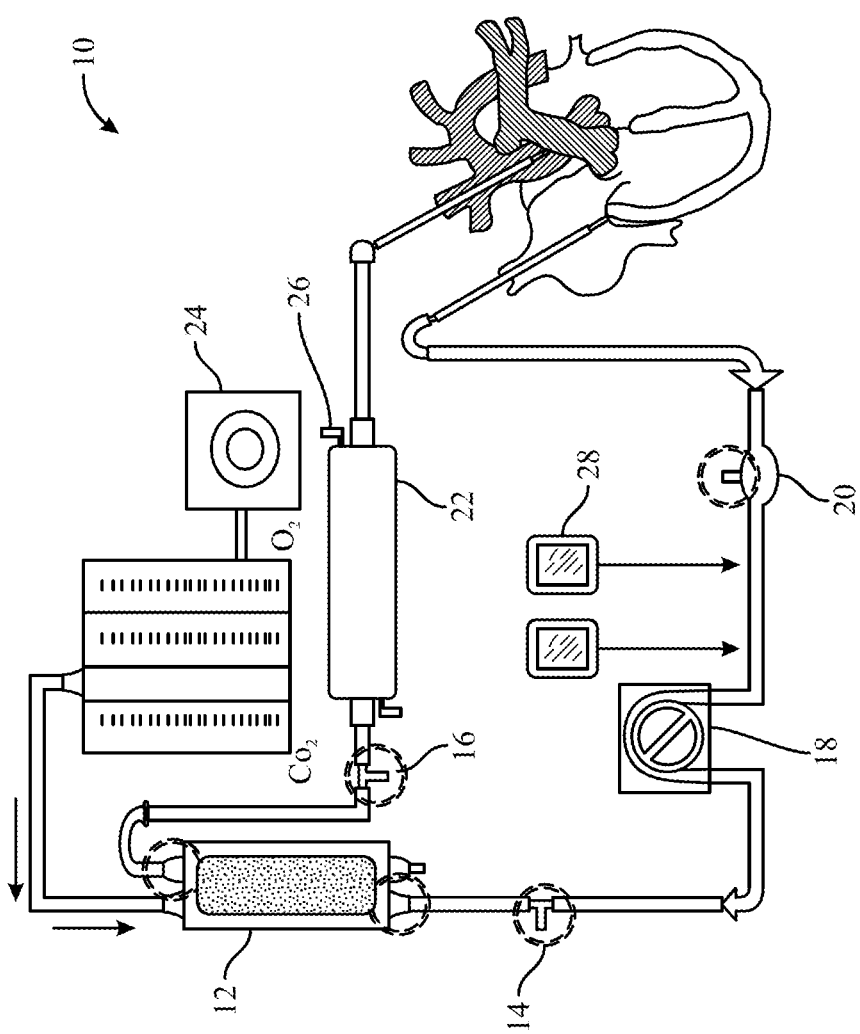
FIG. 1 illustrates a schematic of an ECMO system according to an embodiment.
Figure 2:
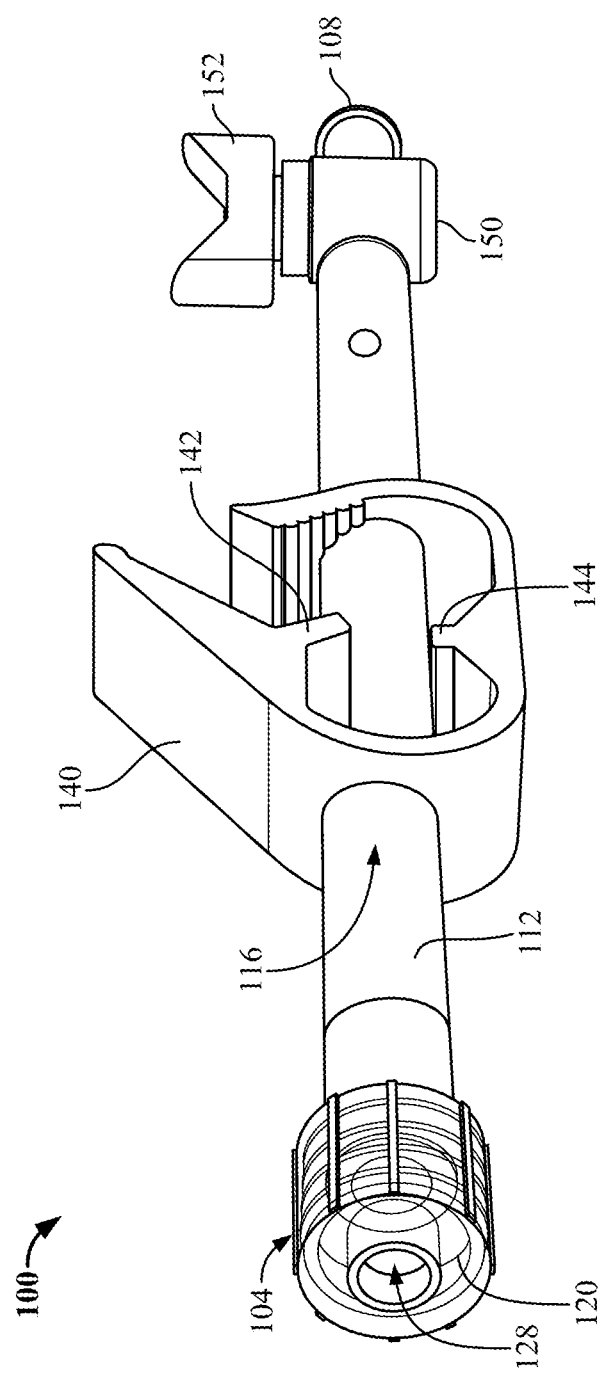
FIG. 2 illustrates an isometric view of a connector assembly according to an embodiment of the present disclosure.
Figure 3:
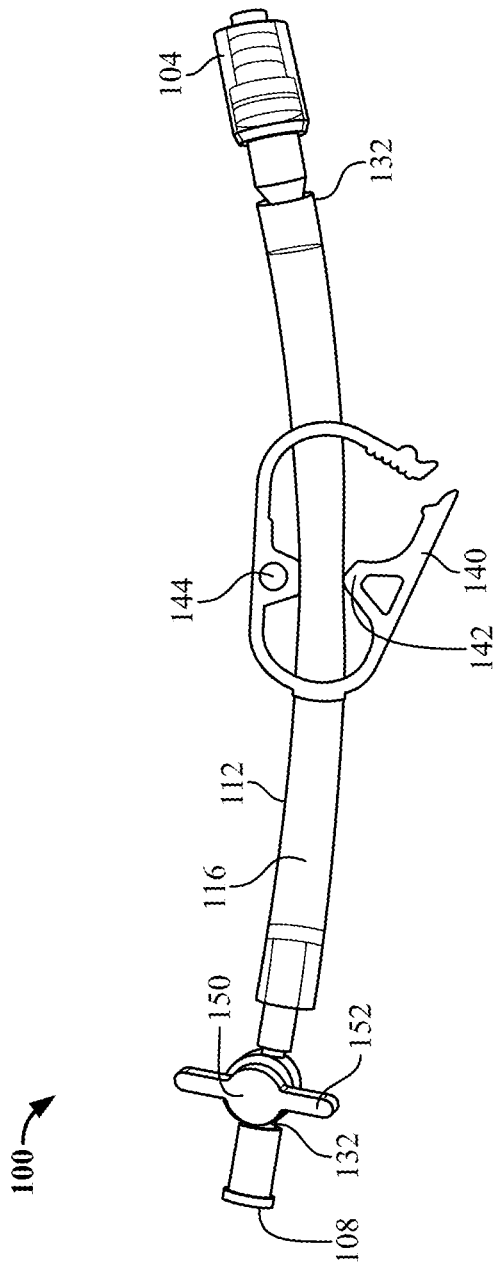
FIG. 3 illustrates a side perspective view of a connector assembly according to an embodiment.
Figure 4:
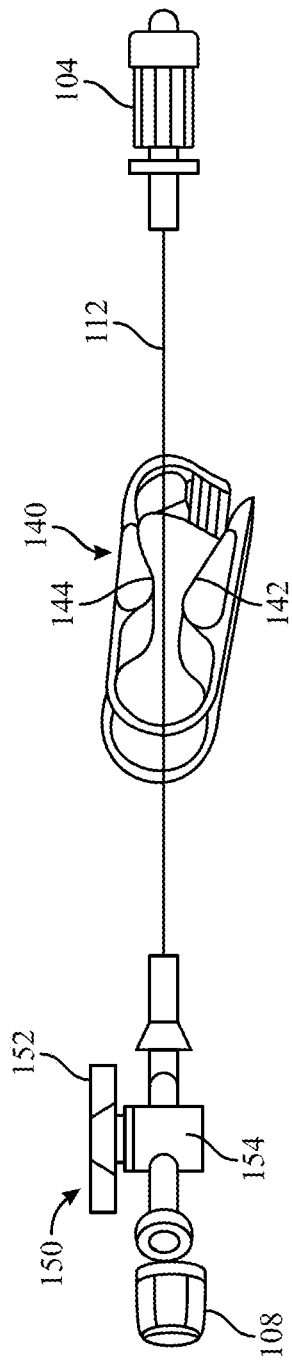
FIG. 4 illustrates a side perspective view of a connector assembly according to an embodiment.
Figure 5:
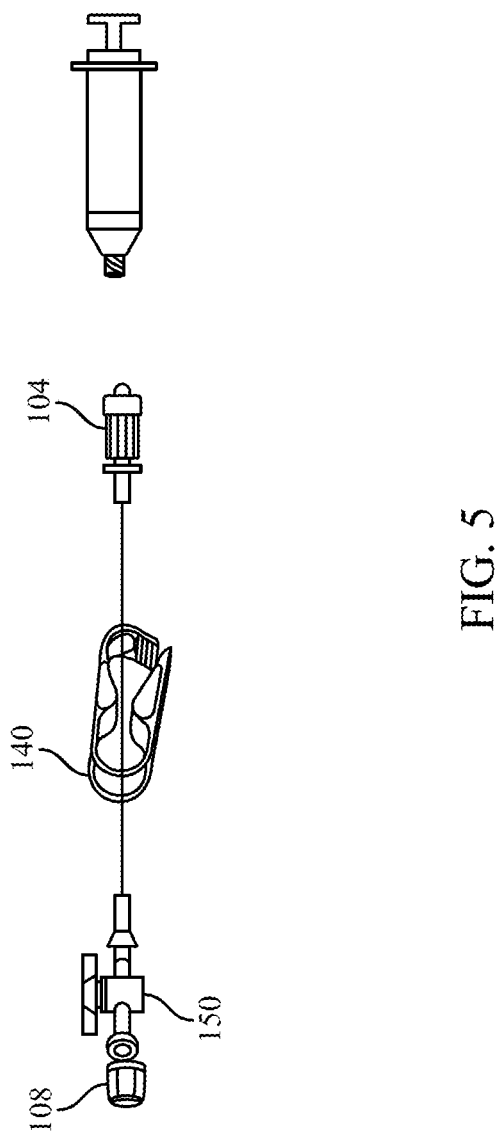
FIG. 5 illustrates a side perspective view of two connector assemblies according to an embodiment.

Aspects of the disclosure will now be described in detail with reference to the drawings, wherein like reference numbers refer to like elements throughout, unless specified otherwise. Certain terminology is used in the following description for convenience only and is not limiting.

The term "plurality," as used herein, means more than one. The singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s" of the claimed invention. Embodiments described in terms of the phrase "comprising" (or its equivalents), also provide, as embodiments, those which are independently described in terms of "consisting of" and "consisting essentially of."

When values are expressed as approximations by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, reference to values stated in ranges includes each and every value within that range.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning as would be understood by those skilled in the relevant art. However, so as to avoid misunderstanding, the meanings of certain terms will be specifically defined or clarified.

The following definitions are intended to assist in understanding the present invention:

The term "biocompatible" is defined to mean the material is capable of coming in contact with physiologic fluids, living tissues, or organisms, without producing unacceptable clinical changes during the time that the material is in contact with the physiologic fluids, living tissues, or organisms.

The term "hemocompatible" is defined as a condition whereby a biocompatible material when placed in contact with whole blood or blood plasma results in clinically acceptable physiologic changes.

As used herein, the term "sorbent" includes adsorbents and absorbents.

The term "hemoperfusion" is defined as passing blood, once through or by way of a suitable extracorporeal circuit, through a device containing the porous polymeric adsorbent to remove toxic molecules from the fluid.

The disclosed methods and devices may be used with any suitable pump-driven or pressure-gradient-driven ECC system, such as extra-corporeal membrane oxygenation (ECMO) systems, CRRT Dialysis, hemoperfusion, cardiopulmonary bypass (CPB), and other similar setups. While specific embodiments may be directed to a particular ECC system (e.g. ECMO), it will be understood that the disclosure is not limited to only the exemplified system.

Referring to exemplary embodiments, an extracorporeal membrane oxygenation (ECMO) system is comprised of numerous components. Some of these components have to be connected to the ECMO system or to each other in such a way as to prevent dangerous conditions from arising during operation of the ECMO system. Once ECMO-based therapy has been started, stopping or slowing down the therapy can lead to a slowdown or stoppage of circulatory support and gas exchange support, which can be detrimental to the patient receiving the therapy. A connector assembly may be used to join various components in the system. The connector assembly presents an interface that allows modifications to the ECMO system and therapy process without having to stop the operation of the ECMO system. An illustrative example of an ECMO system 10 is depicted in FIG. 1 and shows a membrane oxygenator 12, a pre-membrane pressure monitor 14, a post-membrane pressure monitor 16, a pump 18, a venous reservoir 20, a heat exchanger 22, an oxygen blender 24, a warmed water blender input 26, and additional fluid sources 28. It will be understood, however, that various setups and different components may be used in ECMO treatment.

The connector assembly is configured to transport a fluid through itself from a first component attached at one end to a second component attached at another end. The connector assembly can be regulated to permit fluid to flow unobstructed through it, partially impede the flow, or completely obstruct flow, depending on the desired application. Referring to FIGS. 2-5, the connector assembly 100 has a first connection interface 104, and second connection interface 108, and a tubular body 112 extending between the first connection interface 104 and the second connection interface 108. The tubular body 112 has an inner surface that defines a lumen 116 that extends longitudinally along the entire length of the tubular body 112. The lumen 116 is configured to receive fluid and permit movement of the fluid therethrough and out of the lumen 116. The tubular body 112 may include suitable materials typically used in pumping applications. In some embodiments, the materials may need to be biocompatible and capable of being sterilized for use with bodily fluids in a medical procedure. Suitable biocompatible materials, for example, may include thermoplastic elastomers. In embodiments where the material contacts blood or blood components, the material should also be hemocompatible.

Suitable materials for the connector assembly 100 include rubbers and elastomers, for example, but not limited to, ethylene propylene, fluoroelastomer, isobutylene isoprene butyl, isoprene, nitrile rubber, polychloroprene, polyurethane, silicone, and styrene-butadiene. In some applications, materials may include plastics, for example, but not limited to, polyvinyl chloride, chlorinated polyvinyl chloride, high-density polyethylene, low-density polyethylene, and acrylonitrile butadiene styrene. It will be understood that specific materials will vary based on intended application. Certain properties must be considered depending on the intended use and the fluid moved through the connector assembly 100. For example, material interaction with biological components, porosity, gaseous permeability, durability, elasticity, and other specifications of tubing materials.

The connector assembly 100 may include a plurality of connection interfaces. In some embodiments, the connector assembly 100 may have two connection interfaces spaced apart from one another. Still referring to FIGS. 2-5, the first connection interface 104 may be disposed on a proximate end of the tubular body 112, and the second connection interface 108 may be disposed on a distal end of the tubular body 112. The first connection interface 104 and the second connection interface 108 may fluidly communicate with the lumen 116, such that fluid may pass through the first connection interface 104, through the lumen 116, and through the second connection interface 108, or vice versa. In some embodiments, the connector assembly 100 may include a third connection interface, a forth connection interface, or another suitable number of connection interfaces depending on desired application.

Each connection interface may be dimensioned and configured to engage with a component of the connector assembly, an ECMO system, or another suitable system. It will be understood that the connecting mechanism of each connection interface may vary depending on the desired component and connection thereon, and this disclosure is not limited by a particular connection mechanism. Suitable connection mechanisms may include, but are not limited to, Luer lock connectors, slip tip connectors, and other suitable connector types. In some embodiments, each connection interface may have a different connecting mechanism. Alternatively, all connection interfaces in a connector assembly may utilize the same connection mechanism. Referring to the exemplary embodiment of FIG. 3, the first connection interface 104 may include a rotating Luer lock, and the second connection interface 108 may include a slip tip connector.

Each connection interface can engage with another component in the system. In some embodiments, the connection interface may releasably engage directly with a port on another component or indirectly with a tube line leading to one or more components. A particular connection interface may offer various structural advantages. Each connection interface includes a body 120 having a cavity extending therethrough, the cavity defining a passage 128 in fluid communication with the lumen 116. With continued reference to FIGS. 2-5, the first connection interface 104 may be disposed coaxially with the lumen 116 such that the lumen 116 is in fluid communication with the passage 128.

Each connection interface may be attached to the tubular body 112 at an attachment point 132. The first connection interface 104 may be either fixedly or removably attached to the tubular body 112. In some embodiments, the connection interface may be configured to rotate at an attachment point. Referring again to FIGS. 2-5, the first connection interface 104 may attach to the tubular body 112 at the attachment point 132 such that the body 120 of the first connection interface 104 is configured to rotate around its centerline. In some embodiments, the first connection interface 104 may be configured to rotate freely in 360 degrees in either direction. Alternatively, in some embodiments, the range of rotation may be limited to a desired circumferential distance and/or a particular rotational direction.

Having a connection interface that rotates provides for better interaction between the connector assembly and tubes or other components that engage with it via the connection interface. As components and tubes are moved or as they receive a flow of fluid, they may apply a lateral or rotational torsion force on the connection interface. This torsion force can translate to the connected components and tubing itself resulting in twisting or kinking of the tubes. This can lead to obstruction of fluid flow, damage to the tubing and/or components, and accidental disconnection from the connector assembly. On the connector side, the torsion force can twist or turn the connector assembly in various unexpected directions. This can in turn lead to the connector assembly catching on other tubing or components, damage the structural integrity of the tubular body and/or the connection interfaces, kinking or bending of the tubular body, obstructing fluid flow through the tubular body, and accidental disconnections from one or more connection interfaces. In a medical environment, many of the above risks could result in dangerous conditions for the patient, medical professionals, or both. A rotating connection interface may help alleviate these torsion forces by rotating around the attachment point as force is applied. Referring, for example, to the illustrative embodiment of FIG. 3, the first connection interface 104 is configured to rotate, and the second connection interface 108 is configured to be rigidly attached to the connector assembly 100. However, it will be understood that any combination of rotating or fixed connection interfaces would be acceptable depending on the use, manufacturing capabilities, and preference.

In some embodiments, a rotating connection interface may be configured to transition from freely rotating to being in a fixed position. For example, when pressure is applied beyond a predetermined threshold on the connection interface, either inwards to the lumen or out of the lumen (i.e. "positive" or "negative" pressures), the rotating connection interface may temporarily become rigid and resist rotation until the applied pressure drops under the predetermined threshold pressure. This may ensure that a more effective fluid-tight seal is established at the attachment point 132 of the connection interface during fluid movement.

The tubular body 112 and each connection interface may include substantially smooth internal surfaces devoid of bumps, ridges, notches, or other deviations to decrease risk of damage to the fluid passed through the assembly. In some embodiments, the fluid can include blood and blood components, for example plasma, serum, red blood cells, platelets, clotting factors, and other components of human or animal blood. In such embodiments, it may be preferable to have smooth surfaces that contact the blood and/or blood components. Protrusions or notches in the contacting surfaces may cause damage to blood cells causing them to burst (hemolysis), which decreases the number of blood cells returned to the user post treatment. Additionally, discrepancies in the contact surfaces may damage other components in the blood, for example platelets and other clotting components, leading to local coagulation of blood within the assembly. This can result in dangerous conditions for the patient if the clotted blood clogs valves, obstructs fluid flow, or passes from the assembly into the patient.

The connector assembly 100 further includes a plurality of closure mechanisms configured to restrict or terminate fluid flow through the assembly. Still referring to FIGS. 2-5, a first closure mechanism 140 is disposed on the tubular body 112 and is configured to be actuated between an open configuration and a closed configuration. In the open configuration, the first closure mechanism 140 does not obstruct flow through the lumen 116 of the tubular body 112, and in the closed configuration, the first closure mechanism 140 blocks the lumen 116 such that fluid cannot move past the spot of the first closure mechanism 140. In some embodiments, the first closure mechanism 140 is a pinch clamp having a first pinching portion 142 configured to move toward or away from a second pinching portion 144. In the open configuration, the pinch clamp is disposed on the tubular body 112 without blocking the lumen 116. In the closed configuration, the first pinching portion 142 is moved toward the second pinching portion 144 such that the tubular body 112 between the first pinching portion 142 and the second pinching portion 144 is constricted until fluid flow through the lumen 116 is barred. It will be further understood that in embodiments having a pinch clamp, the tubing material used for the tubular body 112 must be rigid enough to withstand repeated stresses associated with pinching and unpinching the tube and flexible enough to be conducive to pinching by the pinch clamp.

A second closure mechanism 150 is disposed on the connector assembly 100 and is configured to be actuated between an open configuration and a closed configuration. In the open configuration, the second closure mechanism 150 does not obstruct flow through the lumen 116 of the tubular body 112, and in the closed configuration, the second closure mechanism 150 blocks the lumen 116 such that fluid cannot move past the spot of the second closure mechanism 150. In some embodiments, the second closure mechanism 150 is a turn valve having an actuator 152 and a blocking element 154. In the open configuration, the actuator 152 is disposed in a first position such that the blocking element 154 does not obstruct the lumen 116. In the closed configuration, the actuator 152 is moved to a second position such that the blocking element 154 completely blocks passage of fluid through the lumen 116. Suitable turn valves may include ball valves, gate valves, or other valve types, and it will be understood that the disclosure is not meant to be limited by the exemplary valves described herein.

The connector assembly 100 may have at least two closure mechanisms, for example the first and second closure mechanisms 140, 150 as described above, but it will be understood that more closure mechanisms may be present, for example three, four, five, or another suitable number of closure mechanisms.

A connector assembly having more than a single closure mechanism provides additional security and assurance that flow through the lumen 116 is shut off when necessary. In some embodiments, external components may be connected to or disconnected from the connector assembly 100. Before connecting or disconnecting any component to or from the connector assembly, it is necessary to ensure that fluid flow through the connector assembly 100 is stopped. In some embodiments, the connector assembly 100 is used in the medical field and carries blood or blood components. It is important to ensure that blood flow through the connector assembly 100 is completely obstructed before disconnecting or removing a connected component or tube. A connector assembly having a single closure mechanism may not provide the same level of security. The single closure mechanism may be damaged and not properly obstruct the lumen. Additionally, a closure mechanism may be inadvertently prematurely moved to the open configuration during operation. Failure of the single closure mechanism can lead to blood loss from the system (and subsequently from the patient), ingress of air or contaminants into the system, and/or exposure to biohazardous material to the environment and the medical staff. Having a second closure mechanism decreases the risk of the above failures. This can create a desired redundancy of closure mechanisms to further reduce chances of a leak or unintended air intake. Additionally, in some embodiments, the first closure mechanism 140 has a different structure from and is configured to operate in a different manner from the second closure mechanism 150, which further decreases chances of accidental opening of the lumen. In the illustrative embodiment of FIGS. 2-5, the first closure mechanism 140 is a pinch clamp, and the second closure mechanism 150 is a turn valve. Pinch clamps are inherently different from turn valves in their structure, mechanism of obstructing the lumen, and actuation from an open configuration to a closed configuration and vice versa.

In some embodiments, the connector assembly 100 may be configured to connect to a blood purification device 200 to supply blood or blood components to or from the blood purification device 200. In some embodiments, the blood purification device 200 may include a cartridge comprising a sorbent material that is configured to purify a fluid material, for example blood or blood components. In some embodiments, the sorbent material may include residues of one or more polymerizable monomers comprising styrene, divinylbenzene, ethylvinylbenzene, acrylate and methacrylate, or other polymerizable monomors suitable for use. Although the disclosure herein refers to a blood purification device, it will be understood that a different component may be used instead of a blood purification device, and that this disclosure is not limited to embodiments that only utilize a blood purification device. Suitable components include, but are not limited to, adsorbers, hemofilters, dialyzers, or other purification devices.

Figure 6:
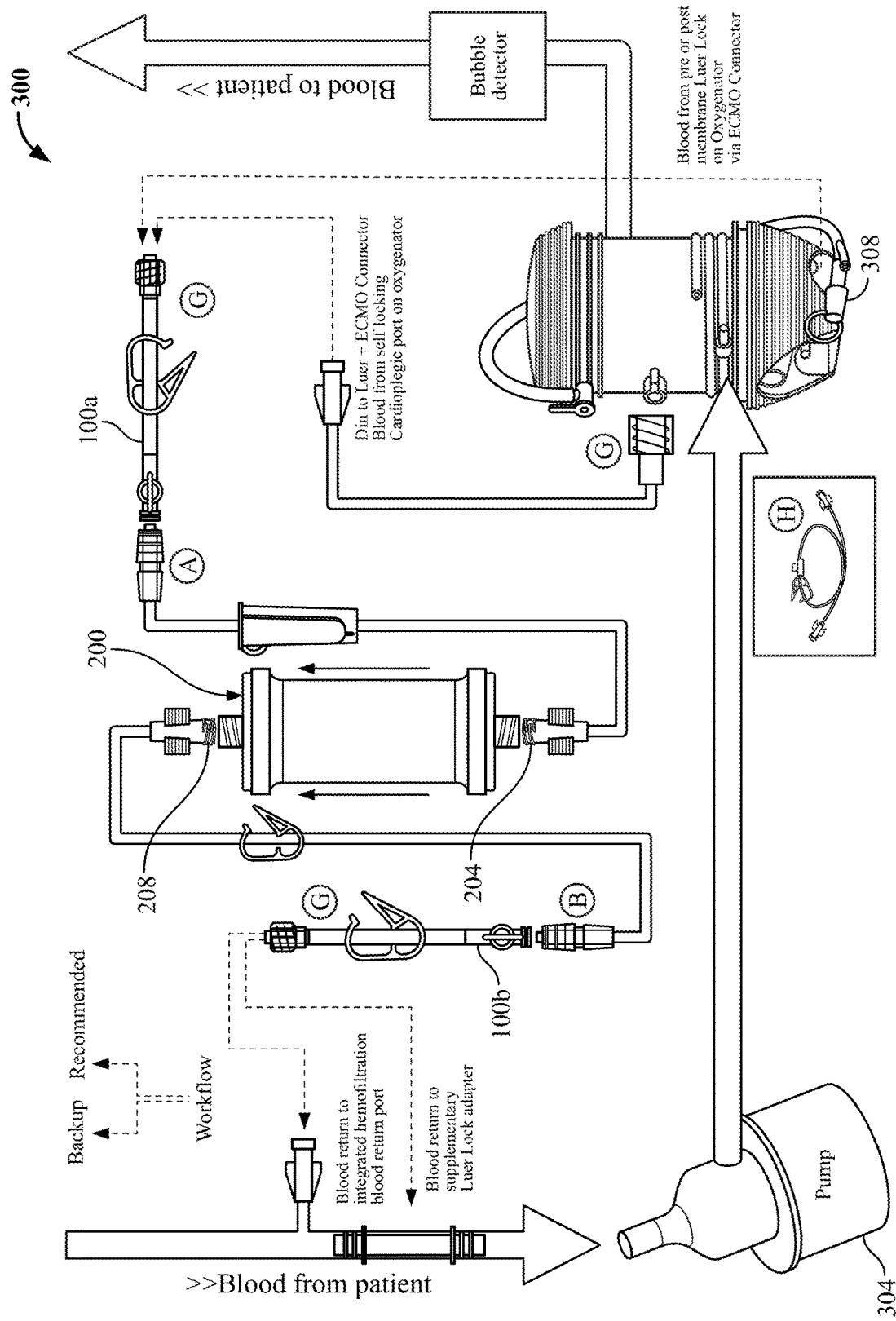
FIG. 6 illustrates a schematic diagram of an ECMO system with a purification device according to an embodiment.

The blood purification device 200 may be a part of or be configured to engage with an extracorporeal membrane oxygenation (ECMO) system 300 having a pump 304 and an oxygenator 308, as illustrated in the exemplary embodiment of FIG. 6. In some embodiments, the blood purification device 200 may be configured to receive a portion of material flowing through the ECMO system 300 and then return purified material back into the ECMO system 300. The blood purification device 200 has an inlet 204 through which material enters the blood purification device 200 and an outlet 208 through which material exits. Each of the inlet 204 and the outlet 208 may be configured to connect to the ECMO system 300 via a separate connector assembly 100. A first connector assembly 100a is disposed between the ECMO system 300 and the inlet 204, and a second connector assembly 100b is disposed between the ECMO system 300 and the outlet 208 of the blood purification device 200.

Figure 7:
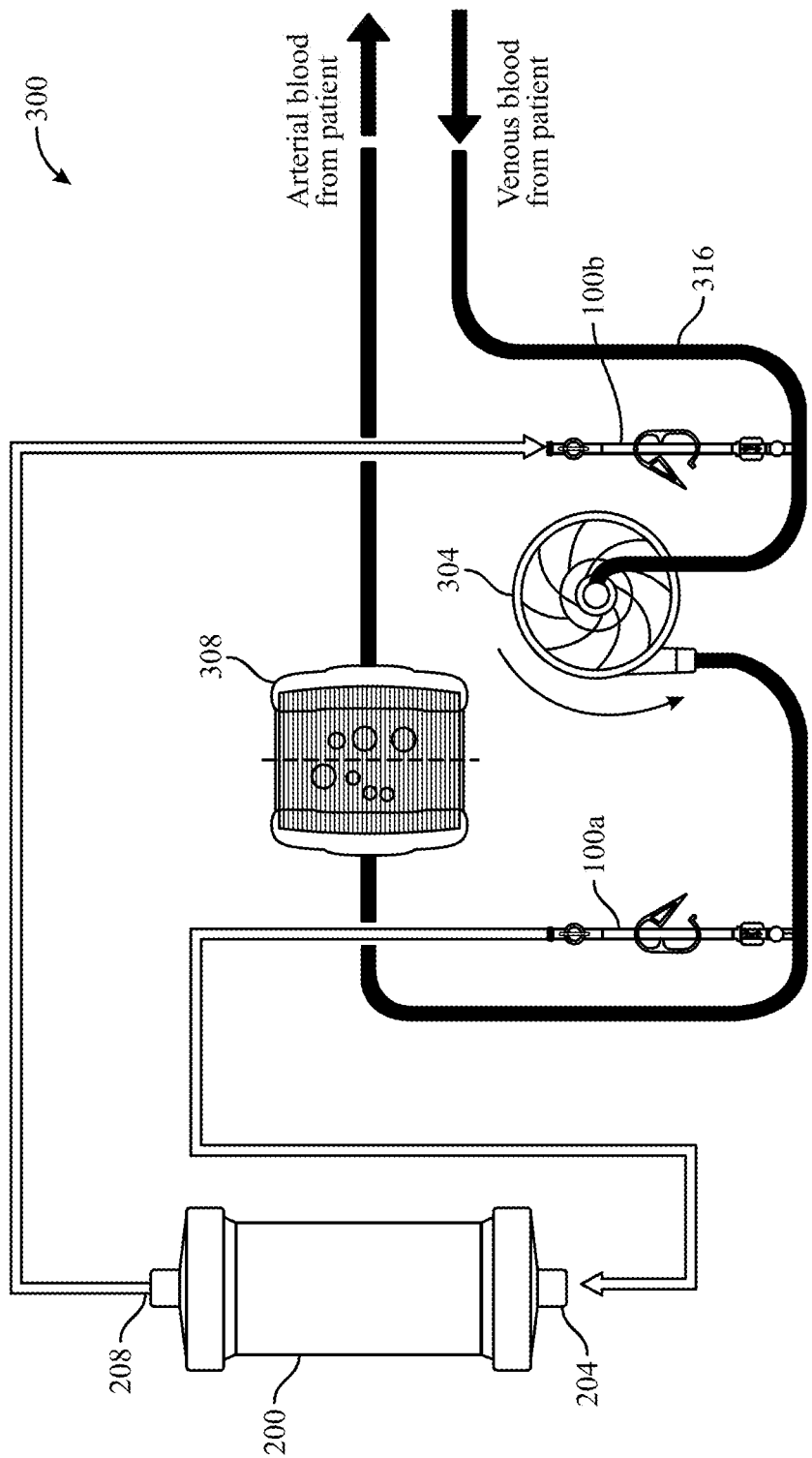
FIG. 7 illustrates an ECMO system with a purification device according to an embodiment.
Figure 8:
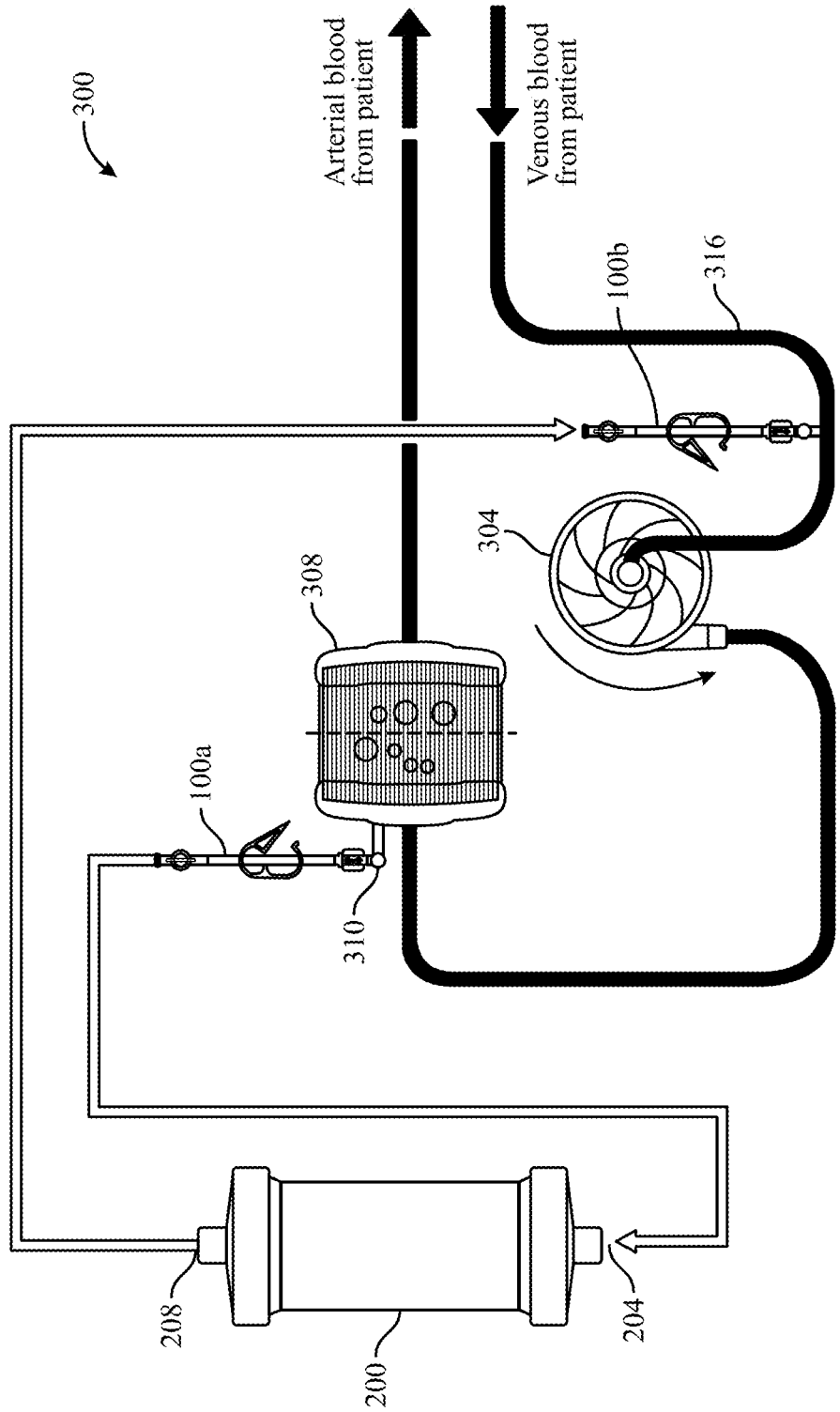
FIG. 8 illustrates an ECMO system with a purification device according to another embodiment.
Figure 9:
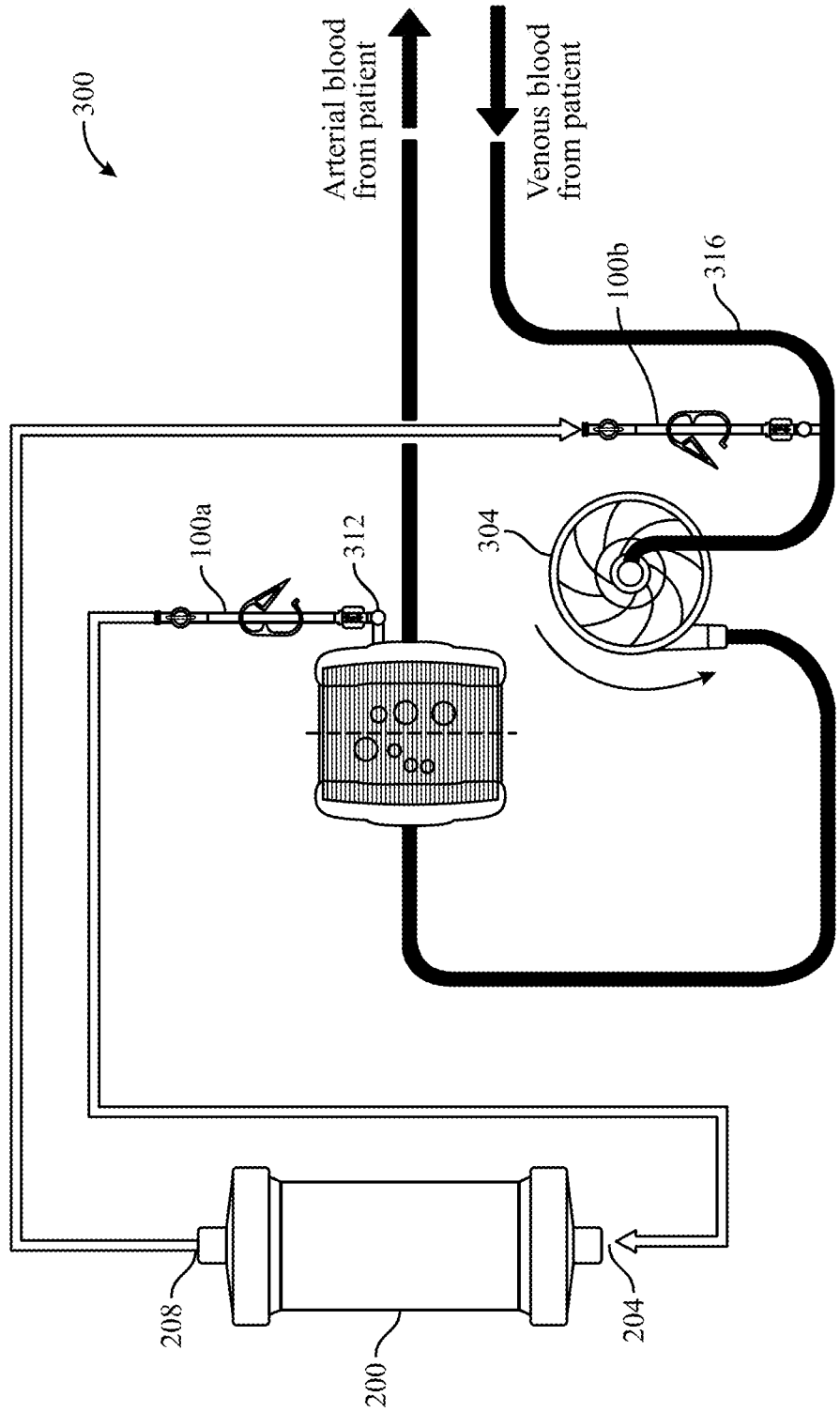
FIG. 9 illustrates an ECMO system with a purification device according to yet another embodiment.

Various arrangements are possible when connecting the blood purification device 200 to the ECMO system 300. In some embodiments, the inlet 204 and outlet 208 of the blood purification device 200 may disposed at different portions of the ECMO system 300 relative to the pump 304 and the oxygenator 308. A passive purification setup is illustrated in FIGS. 7-9, where the first connector assembly 100a is connected to the ECMO system 300 at a location downstream of the pump 304, such that fluid material in the ECMO system 300 passes through the pump 304 before it reaches the first connector assembly 100a. The second connector assembly 100b is disposed upstream of the pump 304, such that fluid material that passes through the blood purification device 200 is introduced back into the ECMO system 300 in such a location that it must then pass through the pump 304 once more.

A passive setup such as described herein may result in faster treatment, as well as lower costs due to fewer necessary materials. Furthermore, due to fewer connections, there exist fewer interfaces of potential leaks, kinds, and other failures that could result in dangerous conditions for the patient and medical staff.

Moreover, the connector assembly 100 is optimized for high flow and includes larger openings than existing alternatives. In some existing connectors, a high fluid flow through the smaller openings and bores results in a high pressure drop as the fluid moves through the system, which results in increased shear stress on the fluid. When used in blood perfusion, the shear stress damages the blood cells and results in hemolysis. The disclosed connector assembly 100, however, allows for higher flow through the connector assembly 100, while reducing the pressure differentials and subsequent shear forces acting on the fluid. This allows for maintaining high flow rates (e.g., approximately 700 ml/min) while decreasing damage to the blood cells and hemolysis.

Figure 10:
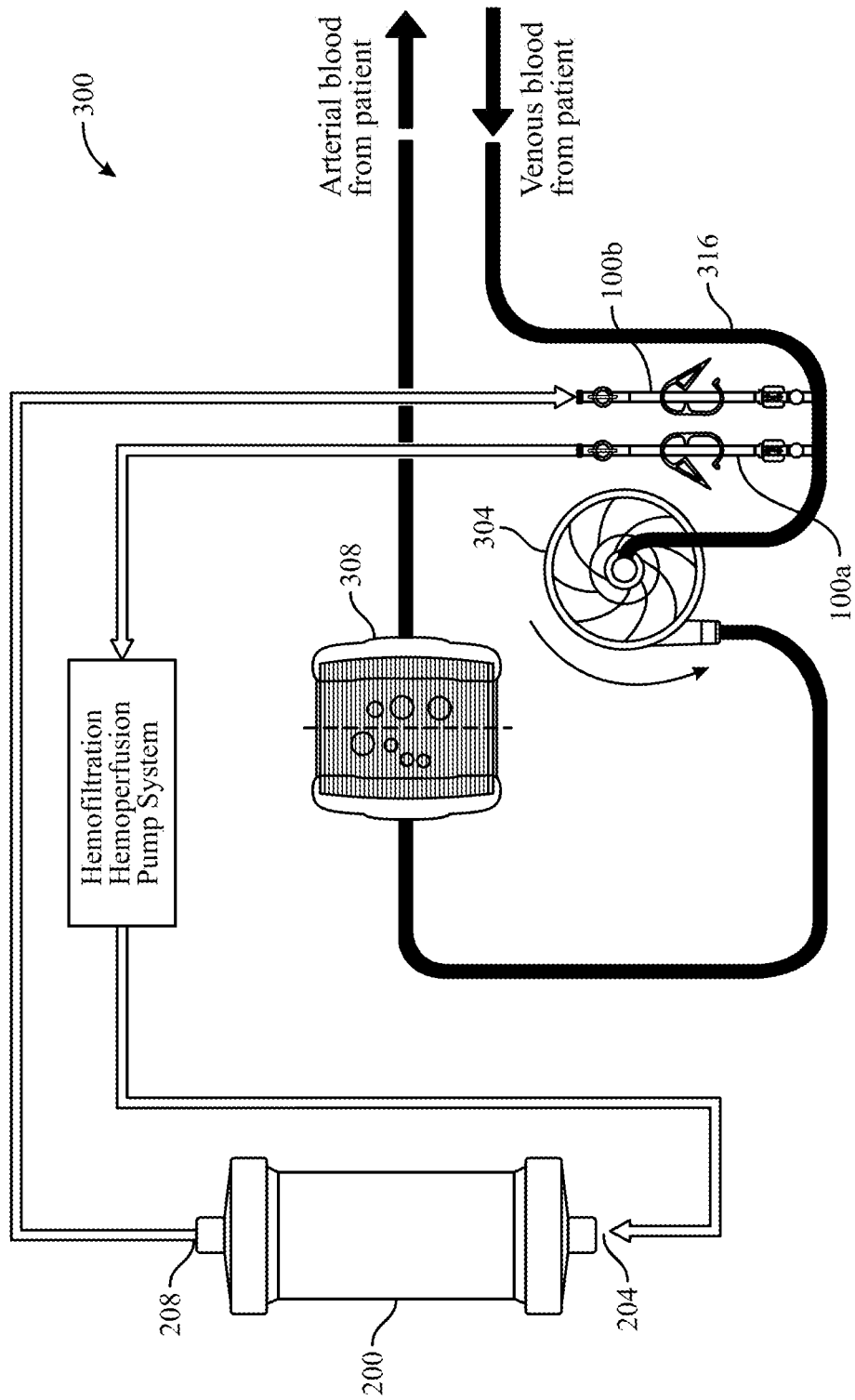
FIG. 10 illustrates an ECMO system with a purification device according to yet another embodiment.
Figure 11:
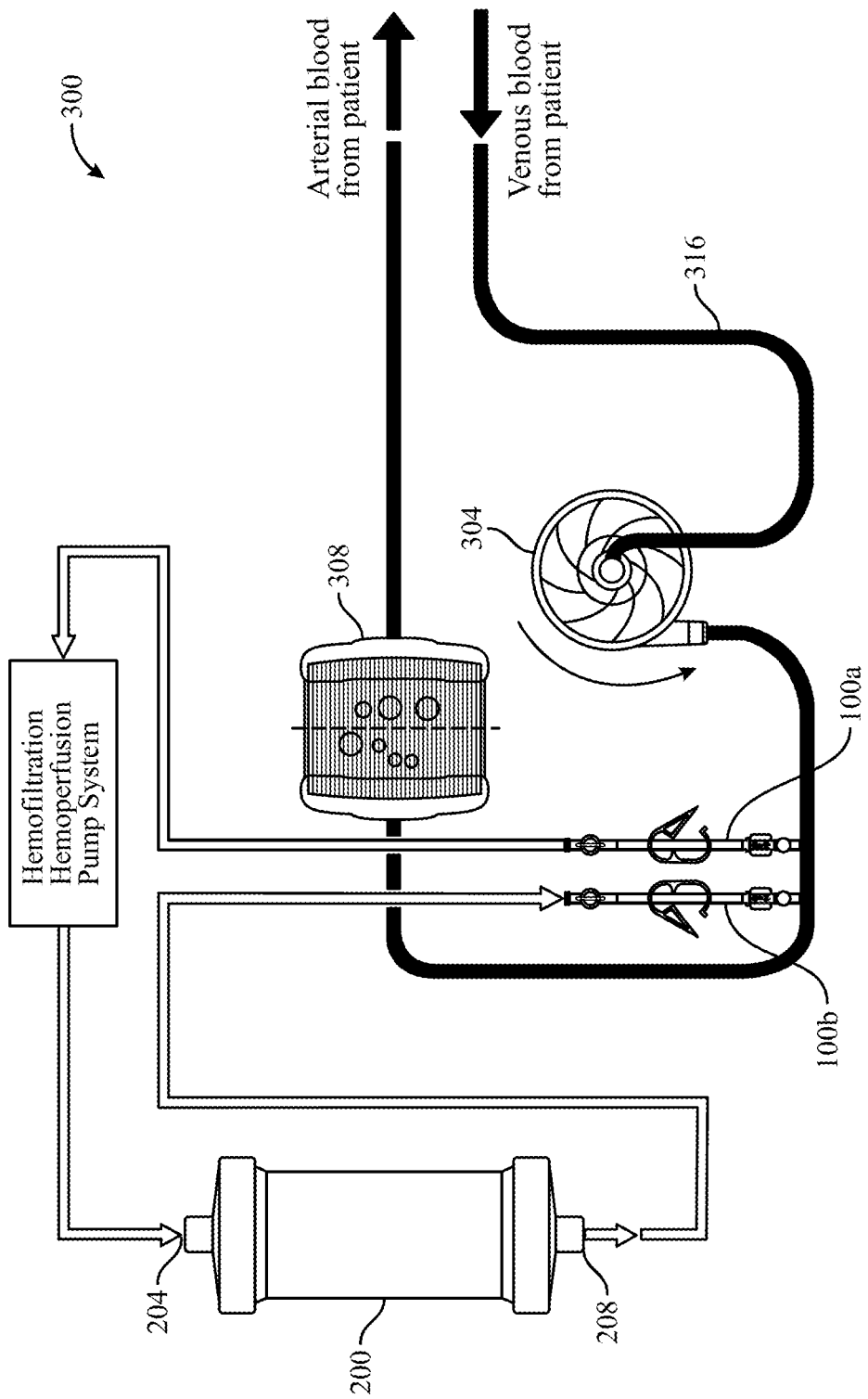
FIG. 11 illustrates an ECMO system with a purification device according to yet another embodiment.
Figure 12:
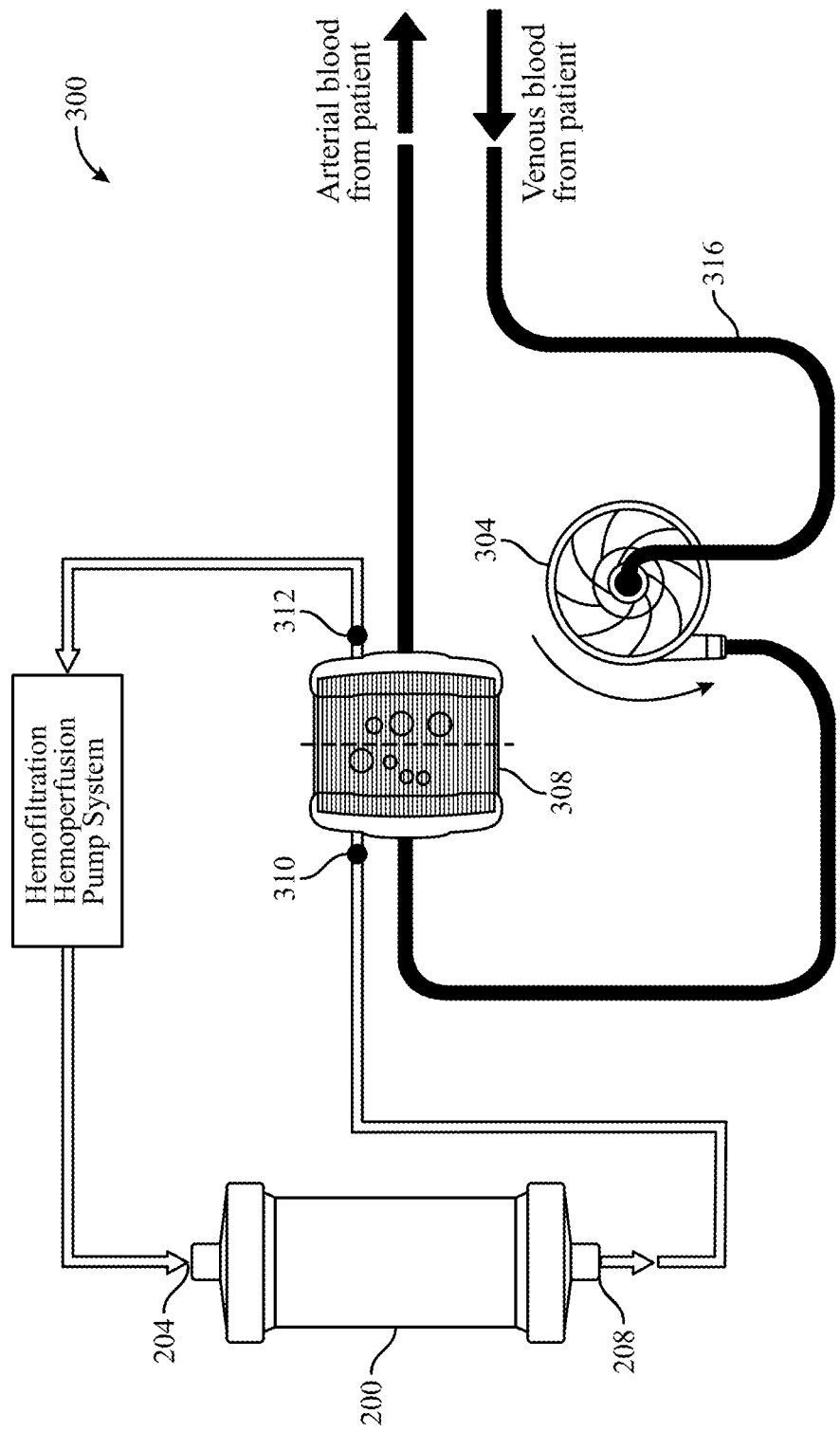
FIG. 12 illustrates an ECMO system with a purification device according to yet another embodiment.

In alternative embodiments shown in FIGS. 10-12, an active purification setup is illustrated. In this embodiment, fluid material is moved from the ECMO system 300 to the blood purification device 200 via a separate pump (not shown). The material undergoes hemofiltration and hemoperfusion and is then returned to the ECMO system 300. Embodiments utilizing an active system may have different connection arrangements. Referring to FIG. 10, for example, the first connector assembly 100a and the second connector assembly 100b, corresponding to the inlet 204 and the outlet 208, respectively, may both be connected to the ECMO system 300 upstream of the pump 304. Alternatively, referring to FIG. 11, the first connector assembly 100a and the second connector assembly 100b may both be connected downstream of the pump 304. In further embodiments, the first connector assembly 100a may be disposed upstream of the pump 304 while the second connector assembly 100b may be disposed downstream of the pump 304, or vice versa.

An active pump setup as described herein offers better customized control over flow rates by controlling the separate pump. Additionally, using an active setup allows for easier integration with existing ECMO systems without requiring difficult or time-consuming modifications. Furthermore, an active setup may lead to lower risks of blood loss or air intake for the patient in the event of failure of purification components. Any elements of the active pump setup or ECMO components that need to be replaced, such as the purification components, may be closed off or removed from the ECMO system while continuing to operate the ECMO system.

Figure 13:
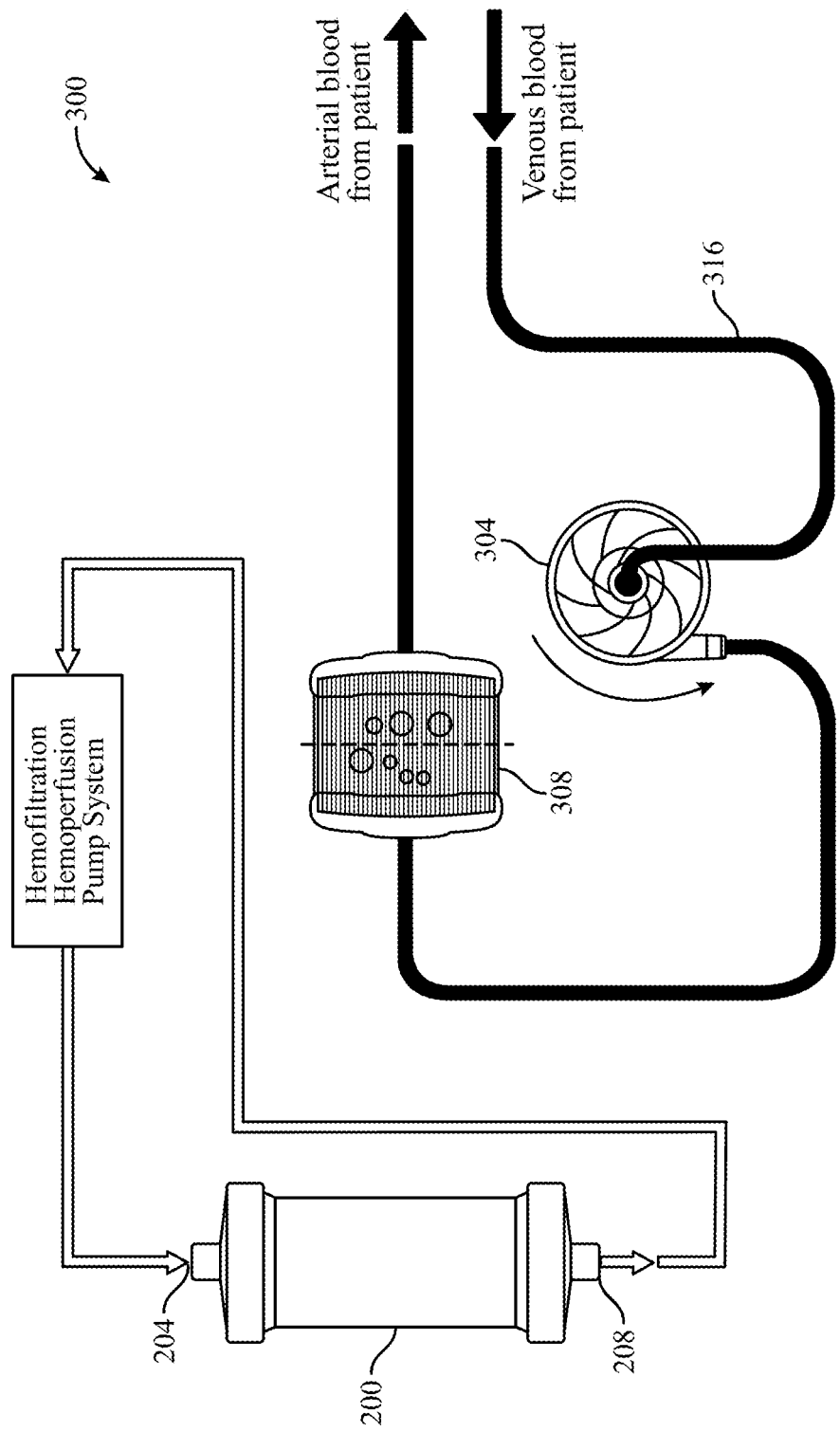
FIG. 13 illustrates an ECMO system and a purification device according to an embodiment.

In some embodiments, the connector assembly 100 may be connected to a connection port on the tubing 316 or on a component of the ECMO system 300, for example on the oxygenator 308. Referring to the illustrative embodiment of FIG. 8, in a passive setup, the first connector assembly 100a may be configured to connect to an upstream port 310 on the oxygenator 308. In an alternative embodiment illustrated in FIG. 9, the first connector assembly 100a may instead be configured to connect to a downstream port 312 on the oxygenator 308. Referring to FIG. 12, in some embodiments utilizing an active setup, the first connector assembly 100a may be configured to connect to the downstream port 312, and the second connector assembly 100b may be configured to connect to the upstream port 310. In further embodiments, the active setup having a blood purification device may be configured to operate independently from the separate ECMO system, as illustrated in the exemplary embodiment of FIG. 13.

Figure 14:
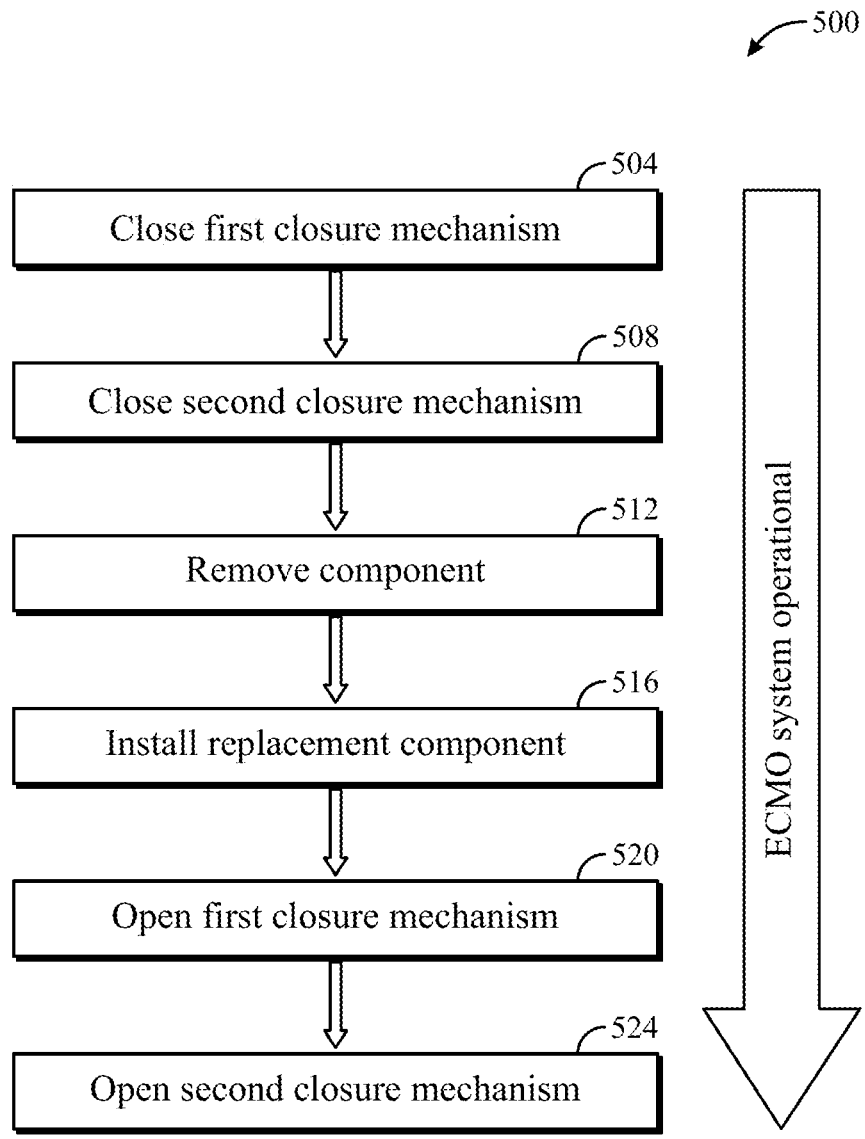
FIG. 14 illustrates a flow chart of a process of operating an ECMO system with a purification device.

In some embodiments, connector assemblies as described herein may be used to facilitate addition, removal, or replacement of components in fluid-flow systems, for example in an ECMO system. FIG. 14 depicts a flow chart showing a process 500 of removing and replacing a component, for example a blood purification device 200, engaged with an ECMO system 300 via a connector assembly 100. The ECMO system is operational during the process and does not need to be stopped. In step 504, the first closure mechanism 140 is moved from the open configuration to the closed configuration. In step 508, the second closure mechanism 150 is moved from the open configuration to the closed configuration. Switching both closure mechanisms obstructs the lumen 116 and prevents liquid and air from passing through the connector assembly 100. In embodiments where the blood purification device 200 is connected to the ECMO system at two points, both closure mechanisms on each connector assembly 100 should be moved to the closed configuration. In some embodiments, it may be advantageous to close both closure mechanisms on the first connector assembly 100a that is connected to the inlet 204 before closing closure mechanisms on the second connector assembly 100b connected to the outlet 208. Moving all closure mechanisms to the closed configuration is necessary to prevent blood loss or air intake. The plurality of closure mechanisms on each connector assembly 100 ensures an obstructed lumen 116 and lowers the risk of accidentally unobstructing the lumen prematurely.

The components described throughout this specification can be manufactured to be easily observed by the user. In some embodiments, the connector assembly 100 may include transparent materials to facilitate inspection of the fluid therein. This can help with detection of foreign objects or air bubbles.

At this stage in the process, the blood purification device 200 is no longer receiving fluid flow from the ECMO system. If the goal is to bypass the blood purification device 200, then the process is complete, and the ECMO system may continue functioning with the closure mechanisms on each connector assembly in the closed configuration. In optional step 512, the blood purification device is physically removed from each connector assembly for proper biohazardous disposal.

Alternatively, in some embodiments, it may be preferable to replace a component, such as the blood purification device 200. In such embodiments, step 512 is necessarily performed to remove the existing component to make room for the replacement component. In step 516, the replacement component is connected to the connector assembly or connector assemblies. It will be understood that the replacement component may be the same as the original component and perform similar tasks, or it may be a different component configured to perform a different job. Once the replacement component has been connected, in step 520, the first closure mechanism is moved from the closed configuration to the open configuration. In step 524, the second closure mechanism is moved from the closed configuration to the open configuration. After steps 520 and 524 have been performed, the lumen 116 in connector assembly 100 is no longer obstructed, and fluid may freely flow through the connector assembly between the ECMO system and the replacement component. If multiple connector assemblies were closed in the preceding steps, then steps 520 and 524 should be repeated for each connector assembly. In some embodiments, portions of the ECMO system and/or original and replacement components may be flushed with a flushing fluid, for example with saline solution, at various stages of the process.

The process described above allows for continuous use of the ECMO system during removal or replacement of one or more components. The continuously-running ECMO system provides necessary support for the patient, and it is beneficial to avoid shutting down operation of the ECMO system during maintenance, such as replacing a component. Because the ECMO system is operational during removal or replacement of components, it is necessary to ensure that fluid moving through the system does not escape the system and air or contaminants do not enter the system due to failures of connection interfaces or closure mechanisms. Replacing a component while the system is operational is also known as "hot-swapping" the component.

In some embodiments, the ECMO system may be continuously operational for many hours or days, for example, between 1 and 24 hours, between 1 and 7 days, between 1 and 14 days, between 1 and 30 days, or for another duration depending on desired treatment.

The ECMO system may be operated at various flow rates depending on preferred setup and predetermined treatments, and the flow rates of the ECMO system affect the flow rates through the connector assemblies and the components connected to the connector assemblies. In some embodiments, the flow rate through the connector assembly may be between about 10 ml/min and about 2000 ml/min, or between about 100 ml/min and about 1000 ml/min, or between about 200 and about 800 ml/, or between about 300 ml/min and about 700 ml/min. In some embodiments, the flow rate through the connector assembly may be about 700 ml/min. It will be understood that flow rates through the connector assembly may vary based on the desired setup, the flow rate of the ECMO system, and on other values, and this disclosure is not intended to be limited to solely the flow rates described above.

While the exemplary aspects describe the aforementioned components in use with an ECMO system, it will be understood that other perfusion systems may be used, and the described components (e.g., the connector assembly 100 and the blood purification device 200) may be incorporated therein. Suitable systems include any pump-driven or pressure-gradient-driven system, such as extra-corporeal circuit (ECC) systems, extra-corporeal membrane oxygenation (ECMO) systems, CRRT Dialysis, hemoperfusion, cardiopulmonary bypass (CPB), and other similar setups.

When one or more components in an ECC (or similar system) needs to be replaced, the entire ECC can be shut down during the replacement process. However, shutting down and restarting a complex system requires many steps (e.g., to ensure sterility) and takes a long time. Additionally, the longer the system is inoperable, the longer the patient is not receiving its benefit. This can lead to health complications for the patient, and/or require the patient to be moved to a different system. This can result in permanent health problems or death for the patient, and can increase duration of the patient's stay in the medical facility and requires more time and professional assistance to achieve the desired treatment.

Figure 15:
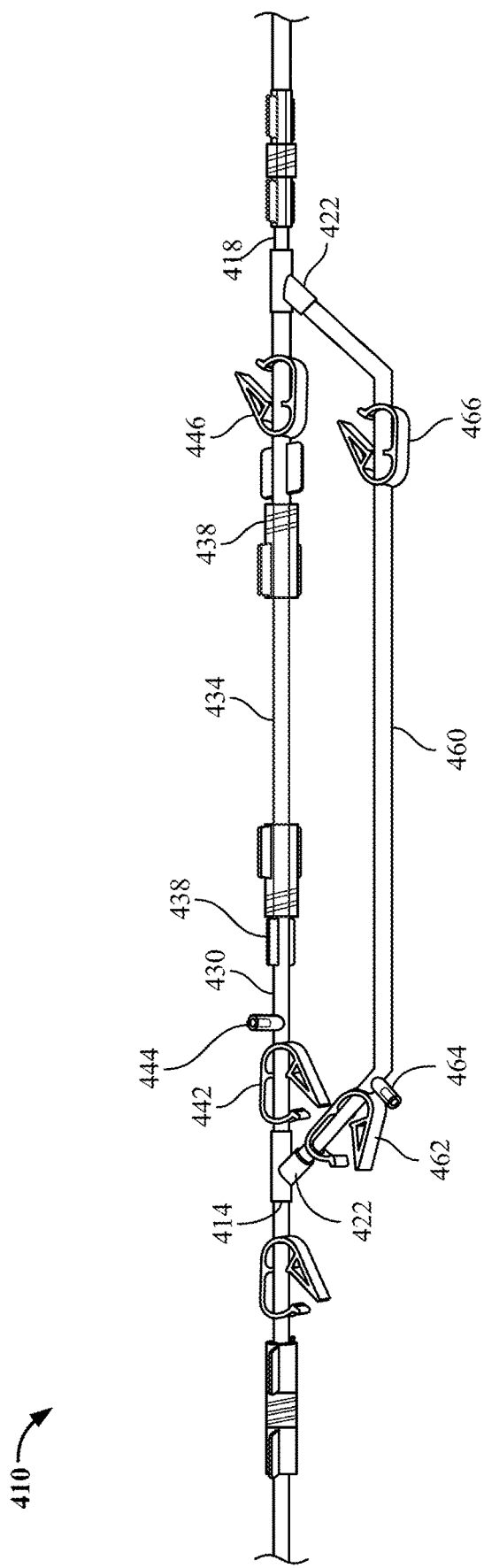
FIG. 15 illustrates a hot-swap assembly according to an embodiment.
Figure 16:
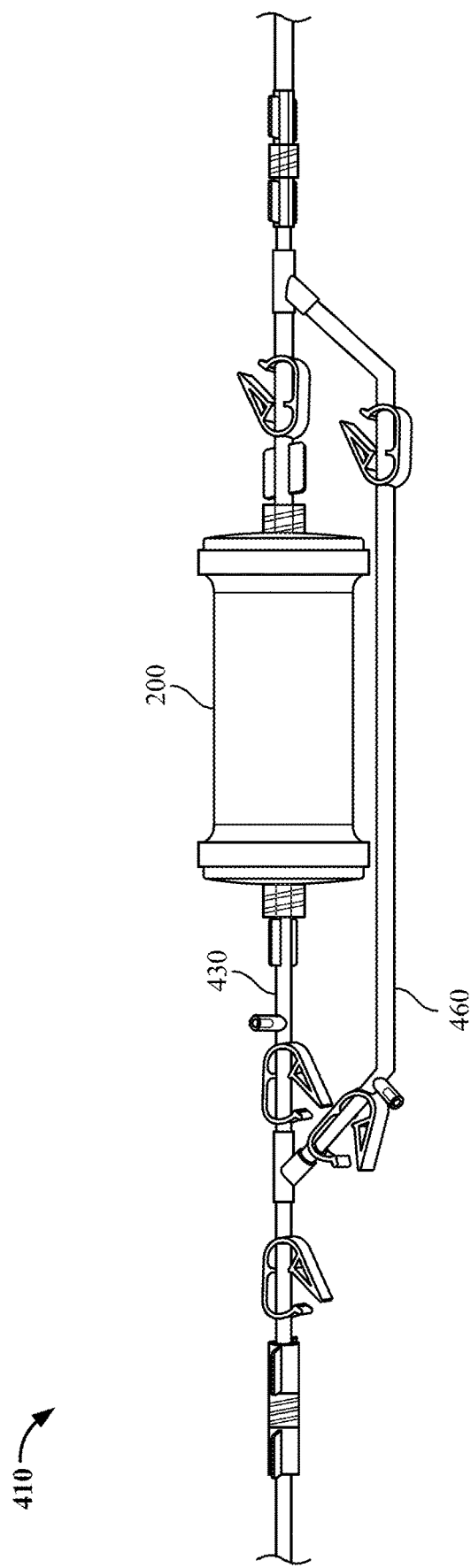
FIG. 16 illustrates a hot-swap assembly according to another embodiment.

In some aspects, it is beneficial to continuously operate the ECC, without pausing or shutting it down, during replacement of a component. Referring to FIGS. 15 and 16, a portion of an ECC system is displayed. The system may include multiple portions of tubing 316 and a hot-swap assembly 410. As depicted in the figures, two sections of tubing 316 may be operatively connected to the hot-swap assembly 410, such that a fluid passage may be established between one of the two sections of tubing 316, through the hot-swap assembly 410, and to the other of the two sections of tubing 316. It will be understood that other arrangements can be made throughout the ECC, and that any suitable number of tubing portions 316 can be utilized. The hot-swap assembly 410 can be coupled with the ECC system or a similar system via one or more suitable connectors. In some embodiments, the hot-swap assembly 410 may connect to the ECC via one, two, or more connector assemblies 100 disclosed throughout this specification.

The hot-swap assembly 410 includes an inlet 414, into which the perfused fluid of the ECC enters the hot-swap assembly 410, and an outlet 418, through which the fluid exits the hot-swap assembly 410. The inlet 414 may include a y-connector 422 for splitting the incoming fluid into two streams. In some aspects, the fluid may be split in more than two streams, and it will be appreciated that a suitable corresponding connector can be used. Multiple fluid pathways can be independently opened or closed as needed.

Similarly, the outlet 418 may include a y-connector 422 for combining two fluids from the hot-swap assembly 410 into a single stream. In some embodiments, it may be advantageous to utilize a y-connector 422 to be allow for flow diversions without stopping the flow. Alternative connectors, for example, a three-way valve, may require the flow to temporarily stop within the active pathway 430 and/or the bypass 460, which, as explained above, is often undesirable for the patient's health.

Multiple fluid pathways extend through the hot-swap assembly 410. Referring again to FIGS. 15 and 16, an active pathway 430 and a bypass 460 each extend between the inlet 414 and the outlet 418. At the inlet 414, the fluid entering the hot-swap assembly 410 is split into two separate streams at the y-connector 422, with one stream being directed towards the active pathway 430, and the other stream being directed towards the bypass 460. Any fluid coming from the separate pathways is recombined into a single fluid at the y-connector 422 disposed at the outlet 418.

Each of the active pathway 430 and the bypass 460 can be configured to receive the fluid from the inlet 414 and pass the fluid therethrough, and to preclude the fluid from entering and/or passing through to the outlet 418. The pathways can be configured such that the active pathway 430 and the bypass 460 are both simultaneously opened and configured to receive the fluid and to pass the fluid therethrough, such that the active pathway 430 is opened while the bypass 460 is closed, such that the active pathway 430 is closed while the bypass 460 is opened, or such that the active pathway 430 and the bypass are both closed.

The active pathway 430 may be configured to receive one or more components typically used in an ECC system. In FIG. 15, the active pathway 430 includes a tube connection 434 disposed between the inlet 414 and the outlet 418. The tube connection 434 may be structurally and/or functionally similar to the tubing 316 disclosed throughout this specification. In some aspects, the tube connection 434 may be removable from the hot-swap assembly 410. As shown in the figures, two connectors 438 may be disposed at either end of the tube connection 434 and may provide a disengageable interface between the tube connection 434 and the active pathway 430, such that when the tube connection 434 is engaged with the active pathway 430, fluid may be permitted to pass through the active pathway 430 from the inlet 414 towards the outlet 418. The connectors 438 may be similar in structure and/or function as any of the connectors described throughout this specification.

The tube connection 434 may be removed from the active pathway 430 by disconnecting the two connectors 438 at both ends. In alternative embodiments, the tube connection 434 may include a single de-coupleable connector 438 at one end and be permanently affixed to, or a part of, the active pathway 430. In such embodiments, the single connector 438 may be disconnected such that the active pathway 430 is interrupted.

When the tube connection 434 is de-coupled from the active pathway 430, another tube connection 434 may be coupled, either in place of or adjacent to, the original tube connection 434. Alternatively, a different component may be coupled. Referring to FIG. 16, a blood purification device 200 may be coupled to the hot-swap assembly 410, such that the blood purification device 200 is disposed within the active pathway 430 between the inlet 414 and the outlet 418. The blood purification device 200 may be configured to engage with and disengage from the same connectors 438 present in the active pathway 430. Although a single component is depicted in the figures, it will be appreciated that multiple components may be attached in series in the active pathway 430, such as multiple blood purification devices 200, multiple tube connections 434, or a combination of the above components.

The active pathway 430 further includes at least one closure mechanism to toggle the active pathway 430 between being open and permitting fluid to pass into and/or out thereof. The active pathway 430 may include a first active clamp 442, disposed closer to the inlet 414 than to the outlet 418, and a second active clamp 446, disposed closer to the outlet 418 than to the inlet 414. The first active clamp 442 may be adjacent to the inlet 414, and the second active clamp 446 may be adjacent to the outlet 418. The first and second active clamps 442, 446 may be similar in structure and/or function to any of the clamps or closure mechanisms described throughout this specification. When the first active clamp 442 is in an open position, fluid is permitted to enter the active pathway 430, and when the first active clamp 442 is in a closed position, fluid is precluded from entering the active pathway 430. When the second active clamp 446 is in an open position, fluid is permitted to exit the active pathway 430 at the outlet 418, and when the second active clamp 446 is in a closed position, fluid is prevented from leaving the active pathway 430. The second active clamp 446, when in the closed position, may also serve to prevent any fluid from moving backwards into the active pathway 430 from the outlet 418 (for example, due to a pressure differential).

The bypass 460 extends from the inlet 414 to the outlet 418, and is configured to have an open configuration, in which fluid is permitted to pass therethrough, and a closed configuration, in which fluid is precluded from entering and/or leaving the bypass 460. The bypass 460 includes at least one closure mechanism to toggle the bypass between the open and closed configurations. As shown in FIGS. 15 and 16, two clamps—a first bypass clamp 462 and a second bypass clamp 466—are disposed on the bypass 460. The first bypass clamp 462 is closer to the inlet 414 than to the outlet 418 and may be adjacent to the inlet 414. The second bypass clamp 466 is closer to the outlet 418 than to the inlet 414 and may be adjacent to the outlet 418. The first and second bypass clamps 462, 466 may be similar in structure and/or function to the first and second active clamps 442, 446 or to any of the other clamps or closure mechanisms described throughout this specification. When the first bypass clamp 462 is in an open position, fluid is permitted to enter the bypass 460, and when the first bypass clamp 462 is in a closed position, fluid is precluded from entering the bypass 460. When the second bypass clamp 466 is in an open position, fluid is permitted to exit the bypass 460 at the outlet 418, and when the second bypass clamp 466 is in a closed position, fluid is prevented from leaving the bypass 460. The second bypass clamp 466, when in the closed position, may also serve to prevent any fluid from moving backwards into the bypass 460 from the outlet 418 (for example, due to a pressure differential).

The hot-swap assembly 410 allows for one or more components in the ECC system to be added, removed, or replaced without ceasing operation of the ECC system. The component to be changed may be disposed in one of the pathways of fluid, for example, in the active pathway 430. While a component is being added, removed, or replaced, the fluid moving through the ECC system may be diverted to one or more pathways absent the specific component. In some embodiments, a blood purification device 200 may be add, removed, or replaced from the active pathway 430. While the blood purification device 200 is being inserted into or removed from the ECC system, the fluid is diverted to a different pathway, for example, the bypass 460.

Figure 18:
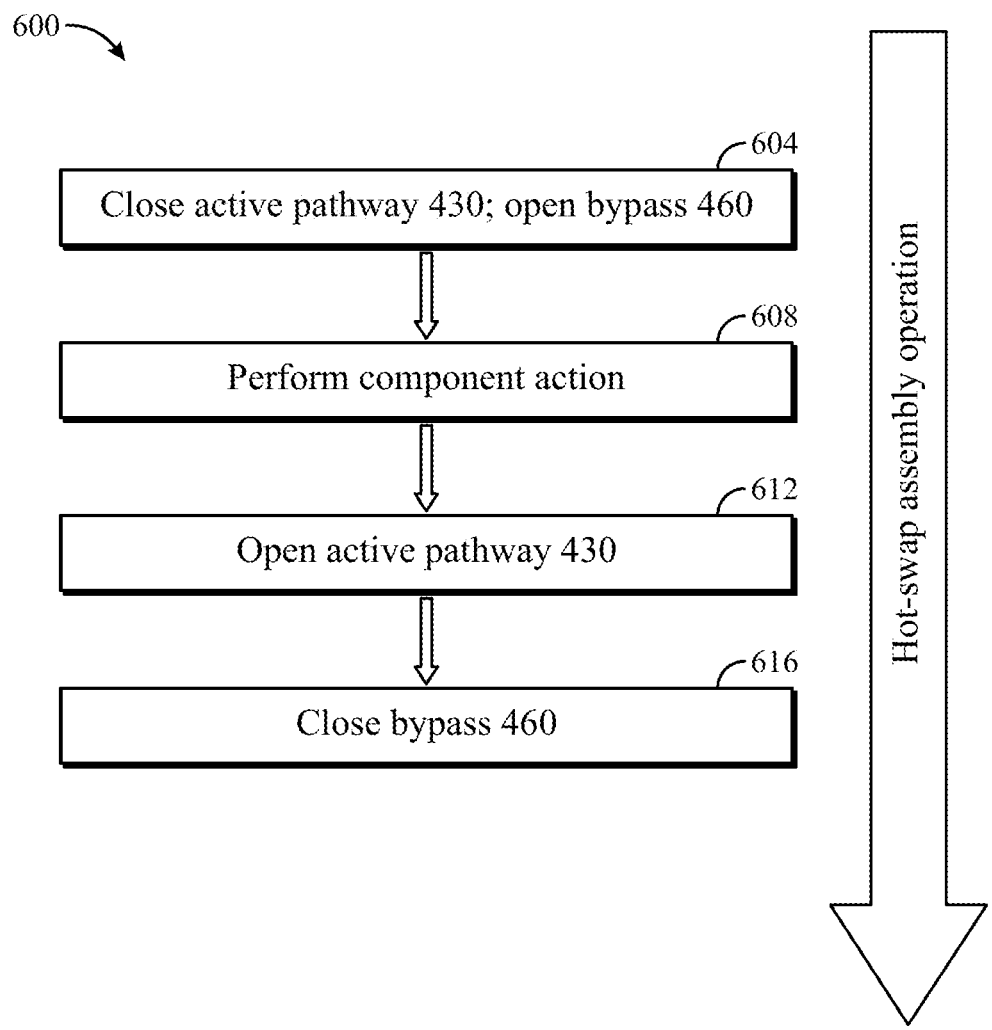
FIG. 18 illustrates a flow chart of a process of performing a hot-swap in an ECC system.

FIG. 18 depicts an exemplary process 600 of operating the hot-swap assembly 410. The process 600 can be utilized with an operating ECC system, or, alternatively, with one that is not running. It will be understood that, if the ECC system is not already operating as necessary, then additional steps may be necessary to start and/or bring the ECC system operation to the desired level before beginning the process 600.

The process 600 begins with step 604, during which the active pathway 430 is closed such that the fluid being pumped by the ECC system is precluded from entering the active pathway 430 at the inlet 414. When the active pathway 430 is closed, the fluid passes instead to the bypass 460. Referring to the specific embodiments described throughout this specification and depicted in the figures, the active pathway 430 may be closed by first moving the first active clamp 442 from the open configuration to the closed configuration, and then by moving the second active clamp 446 from the open configuration to the closed configuration. An intermediate flushing step may be performed before closing the second active clamp 446. In the flushing step, the active pathway 430 is flushed with a suitable flushing fluid (e.g., saline) towards the outlet 418. After closing the second active clamp 446, the first active clamp 442 may be opened and a flushing step may be performed in the active pathway 430 in the direction of the inlet 414, after which the first active clamp 442 is again closed. At this point, the active pathway 430 is closed to prevent fluid from entering it at the inlet 414 or leaving it at the outlet 418.

If the bypass 460 is not in the open configuration at the time of closure of the active pathway 430, the bypass 460 is opened. It may be beneficial to open the bypass 460 right before or simultaneously with closing the active pathway 430. This allows the fluid to move through the hot-swap assembly 410 without significant interruption during the process 600. This avoids unnecessary stoppage of fluid flow or a build-up of pressure due to closure of both pathways, both of which could lead to complications for the patient.

After the active pathway 430 has been closed and fluid is no longer traveling therethrough, the desired component swapping action may be performed in step 608. As described above, suitable actions may include adding or removing one or more components in-line with the active pathway 430. For example, a tube connection 434 may be coupled to the active pathway 430 or de-coupled therefrom. Additionally, or alternatively, a blood purification device 200 may be coupled into the active pathway 430, either in place of or in addition to another component. If a component is to be replaced, the existing component (e.g. blood purification device 200) is de-coupled, and the replacement component is coupled in its place.

After the desired component action has been completed in step 608, the active pathway 430 is opened in step 612. The first and second active clamps 442, 446 are moved from the closed position to the open positions, and fluid can then enter the active pathway 430 at the inlet 414 and travel toward the outlet 418.

After the active pathway 430 has been re-opened, the bypass 460 is closed in step 616. To close the bypass 460, the first and second bypass clamps 462, 466 are moved from the open positions to the closed positions. This prevents fluid from entering the bypass 460 and instead directs it to the active pathway 430, such that all of the fluid is moved through the active pathway 430 and passes through the components therein (e.g., the blood purification device 200).

Furthermore, a flushing of the bypass 460 can be performed. After both the first and second bypass clamps 462, 466 have been closed, the second bypass clamp 466 may be opened, and the bypass 460 can be flushed with suitable flushing fluid in the direction of the outlet 418. The second bypass clamp 466 is then closed, and the first bypass clamp 462 is opened. The bypass 460 is then flushed in the opposite direction towards the inlet 414, after which the first bypass clamp 462 is also closed.

Figure 17:
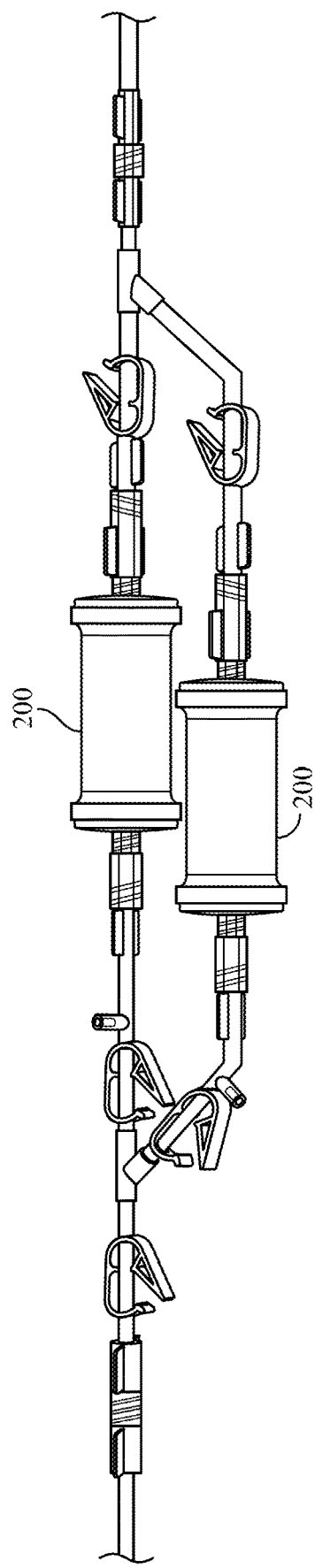
FIG. 17 illustrates a hot-swap assembly according to yet another embodiment.

The flushing can be performed in any suitable way, for example, by introducing a flushing syringe (not shown) into a port along the active pathway 430 and bypass 460. The port may include a self-sealing valve that is configured to open only when it interacts with a suitable connector. The flushing syringe and the port may have a Luer-type interface and be configured to engage with each other for the duration of the flushing step. In some embodiments, a flushing line (not shown) can be permanently connected to the ports. Referring to FIGS. 15-17, an active pathway port 444, disposed between the first and second active clamps 442, 446, may be configured to receive a flushing syringe to perform a flushing step of the active pathway 430. Similarly, a bypass port 464, disposed between the first and second bypass clamps 462, 466, may be configured to receive a flushing syringe to perform a flushing step of the bypass 460.

The flushing steps serve to remove fluid (e.g., blood) from the flushed pathway. The disposition of the active pathway port 444 between the first and second active clamps 442, 446 and the bypass port 464 between the first and second bypass clamps 462, 466 allows for both, forward and backward flushing of the active pathway 430 and the bypass 460, respectively. Forward flushing can be defined as flushing of the active pathway 430 or bypass 460 in the direction of the second active clamp 446 or second bypass clamp 466, respectively, and backward flushing can be defined as flushing in the opposite direction toward the first active clamp 442 or first bypass clamp 462, respectively.

In some embodiments, the flushing steps are important to the therapy and for properly and safely operating the ECC system. If blood within the ECC system is not effectively removed, the system may sustain damage. Additionally, the patient receiving the therapy may experience adverse health effects, such as blood clots, infection, or insufficient blood volume.

In some embodiments, the hot-swap assembly 410 may include multiple active pathways 430, each of those being configured to couple with, or de-couple from, one or more components. Referring to FIG. 17, two separate active pathways 430 may each include a blood purification device 200. In such embodiments, when a hot-swap process needs to be performed on one of the active pathways 430, the one or more other active pathways can operate as a bypass 460. This would allow for not only continuous operation of an ECC system, even when a blood purification device 200 is being removed or replaced within the active pathway 430, but would allow for continuous filtration through at least one blood purification device 200 even during the hot-swap process 600 described above.

While the disclosure has been described in connection with the various embodiments of the various figures, it will be appreciated by those skilled in the art that changes could be made to the embodiments described above without departing from the broad inventive concept thereof. It is understood, therefore, that this disclosure is not limited to the particular embodiments disclosed, and it is intended to cover modifications within the spirit and scope of the present disclosure as defined by the claims.

Features of the disclosure that are described above in the context of separate embodiments may be provided in combination in a single embodiment. Conversely, various features of the disclosure that are described in the context of a single embodiment may also be provided separately or in any sub-combination. Finally, while an embodiment may be described as part of a series of steps or part of a more general structure, each said step may also be considered an independent embodiment in itself, combinable with others.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

What is claimed:

1. A method of modifying a component in an extracorporeal membrane oxygenation (ECMO) system during operation of the ECMO system, the component being in fluid communication with a connector having a tubular body with an inner surface that defines a lumen extending therethrough, wherein the ECMO system comprises an active bypass extending between an inlet and an outlet, and an active pathway extending between the inlet and the outlet and in fluid communication with the lumen, the connector having a first closure mechanism and a second closure mechanism and a connection interface engaged with the component, and the active bypass having a first bypass closure mechanism and a second bypass closure mechanism, wherein each of the first and second closure mechanisms are configured to have an open configuration in which the first and second closure mechanisms, respectively, do not obstruct the lumen and a closed configuration in which the first and second closure mechanisms, respectively, obstruct the active bypass, and wherein each of the first and second bypass closure mechanisms are configured to have an open configuration in which the first and second bypass closure mechanisms, respectively, do not obstruct the active bypass and a closed configuration in which the first and second bypass closure mechanisms, respectively, obstruct the active bypass, the method comprising:
opening the active bypass such that fluid flows simultaneously through the active bypass and the active pathway from the inlet to the outlet, wherein opening the active bypass includes switching the first bypass closure mechanism from the closed configuration to the open configuration such that fluid flows into the active bypass at the inlet, and switching the second bypass closure mechanism from the closed configuration to the open configuration such that fluid flows out of the active bypass at the outlet;

closing the active pathway while fluid flows through the active bypass from the inlet to the outlet, wherein closing the active pathway includes switching the first closure mechanism from the open configuration to the closed configuration such that fluid flow through the lumen is obstructed by the first closure mechanism, and switching the second closure mechanism from the open configuration to the closed configuration such that fluid flow through the lumen is obstructed by the second closure mechanism; and disconnecting the component from the ECMO system by disengaging the component from the connection interface of the connector;

wherein switching the first closure mechanism comprises switching a pinch clamp from an open configuration to a closed configuration and switching the second closure mechanism comprises turning a turn valve from an open configuration to a closed configuration.

2. The method of claim 1, further comprising flushing at least a portion of the ECMO system with fluid containing saline.

3. The method of claim 1, further comprising operating the ECMO system continuously for up to 30 days.

4. The method of claim 1, wherein the fluid includes blood plasma.

5. The method of claim 1, wherein the component is a cartridge having a sorbent material.

6. The method of claim 1, wherein the sorbent material includes residues of one or more polymerizable monomers comprising styrene, divinylbenzene, ethylvinylbenzene, acrylate and methacrylate.

7. The method of claim 1, further comprising a bypass port disposed between the first bypass closure mechanism and the outlet, the bypass port configured to receive a flushing syringe to flush the active bypass.

8. The method of claim 1, further comprising:
connecting the replacement component to the ECMO system;
switching the first closure mechanism from the closed configuration to the open configuration such that fluid may flow through the lumen past the first closure mechanism; and
switching the second closure mechanism from the closed configuration to the open configuration such that fluid may flow through the lumen past the second closure mechanism.

9. The method of claim 8, wherein the replacement component is a replacement cartridge having a sorbent material.

10. The method of claim 1, further comprising operating the ECMO system to move fluid through the lumen at between about 10 ml/min to about 2000 ml/min.

11. The method of claim 10, further comprising operating the ECMO system to move fluid through the lumen at between about 100 ml/min to about 1000 ml/min.

12. The method of claim 11, further comprising operating the ECMO system to move fluid through the lumen at between about 200 and about 800 ml/min.

13. The method of claim 1, wherein the active pathway further comprises a first active closure mechanism configured to obstruct the active pathway when the first active closure mechanism is in a closed configuration.

14. The method of claim 13, wherein the first active closure mechanism is disposed between the inlet and the component.

15. The method of claim 13, further comprising an active pathway port disposed between the first active closure mechanism and the component, the active pathway port configured to receive a flushing syringe to flush the active pathway.

16. The method of claim 13, wherein the active pathway further comprises a second active closure mechanism configured to obstruct the active pathway when the second active closure mechanism is in a closed configuration.

17. The method of claim 16, wherein the second active closure mechanism is disposed between the outlet and the component.

* * * * *